United States Patent
Chang et al.

(10) Patent No.: US 6,950,546 B2
(45) Date of Patent: Sep. 27, 2005

(54) APPARATUS AND METHOD FOR DETECTING SURFACE DEFECTS ON A WORKPIECE SUCH AS A ROLLED/DRAWN METAL BAR

(75) Inventors: Tzyy-Shuh Chang, Ann Arbor, MI (US); Daniel Gutchess, Saline, MI (US); Hsun-Hau Huang, Ann Arbor, MI (US)

(73) Assignee: OG Technologies, Inc., Ann Arbor, MI (US)

( * ) Notice: Subject to any disclaimer, the term of this patent is extended or adjusted under 35 U.S.C. 154(b) by 341 days.

(21) Appl. No.: 10/331,050

(22) Filed: Dec. 27, 2002

(65) Prior Publication Data

US 2004/0105001 A1 Jun. 3, 2004

Related U.S. Application Data

(60) Provisional application No. 60/430,549, filed on Dec. 3, 2002.

(51) Int. Cl.[7] .................................................. G06K 9/00
(52) U.S. Cl. ........................ 382/141; 382/108; 382/152
(58) Field of Search ................................ 382/108, 152, 382/141–143; 348/86; 250/559.18; 356/430, 71

(56) References Cited

U.S. PATENT DOCUMENTS

| | | |
|---|---|---|
| 3,933,532 A | 1/1976 | Glomb |
| 4,118,732 A | 10/1978 | Ichijima et al. |
| 4,121,294 A | 10/1978 | Galanis et al. |
| 4,127,815 A | 11/1978 | Vild et al. |
| 4,139,890 A | 2/1979 | Yerkes et al. |
| 4,141,071 A | 2/1979 | Yerkes et al. |
| 4,219,844 A | 8/1980 | Ohsumi et al. |
| 4,223,346 A | 9/1980 | Neiheisel et al. |
| 4,237,959 A | 12/1980 | Yamamoto et al. |
| 4,319,270 A | 3/1982 | Kimura et al. |
| 4,338,822 A | 7/1982 | Yamaguchi et al. |
| 4,377,238 A * | 3/1983 | Wilks et al. ................. 209/587 |
| 4,461,995 A | 7/1984 | Harris |
| 4,493,859 A | 1/1985 | Krantz |
| 4,495,587 A | 1/1985 | Plante et al. |
| 4,519,041 A | 5/1985 | Fant et al. |
| 4,534,405 A | 8/1985 | Hulek et al. |
| 4,561,104 A | 12/1985 | Martin |
| 4,635,111 A * | 1/1987 | Moore ......................... 348/131 |
| 4,665,317 A | 5/1987 | Ferriere et al. |
| 4,759,072 A | 7/1988 | Yamane et al. |
| 4,837,510 A | 6/1989 | Tornblom |
| 4,853,634 A | 8/1989 | Tornblom |
| 4,926,928 A | 5/1990 | Leckie |
| 5,068,799 A | 11/1991 | Jarrett, Jr. |
| 5,101,461 A * | 3/1992 | Nakajima ..................... 385/42 |
| 5,103,722 A | 4/1992 | Brengman et al. |
| 5,146,311 A | 9/1992 | Chang |

(Continued)

*Primary Examiner*—Amelia M. Au
*Assistant Examiner*—Wes Tucker
(74) *Attorney, Agent, or Firm*—Dykema Gossett PLLC (57) ABSTRACT

The present invention is directed to solving the problems associated with the detection of surface defects on metal bars as well as the problems associated with applying metal flat inspection systems to metal bars for non-destructive surface defects detection. A specially designed imaging system, which is comprised of a computing unit, line lights and high data rate line scan cameras, is developed for the aforementioned purpose. The target application is the metal bars (1) that have a circumference/cross-section-area ratio equal to or smaller than 4.25 when the cross section area is unity for the given shape, (2) whose cross-sections are round, oval, or in the shape of a polygon, and (3) are manufactured by mechanically cross-section reduction processes. The said metal can be steel, stainless steel, aluminum, copper, bronze, titanium, nickel, and so forth, and/or their alloys. The said metal bars can be at the temperature when they are being manufactured.

2 Claims, 5 Drawing Sheets

U.S. PATENT DOCUMENTS

| | | |
|---|---|---|
| 5,363,901 A | 11/1994 | Bjornestol et al. |
| 5,442,285 A | 8/1995 | Zombo et al. |
| 5,654,977 A * | 8/1997 | Morris .......................... 374/4 |
| 5,866,820 A | 2/1999 | Camplin et al. |
| 6,002,251 A | 12/1999 | Sun |
| 6,092,059 A | 7/2000 | Straforini et al. |
| 6,184,924 B1 | 2/2001 | Schneider et al. |
| 6,597,455 B1 * | 7/2003 | Wlodarski et al. .......... 356/430 |

* cited by examiner

APPARATUS AND METHOD FOR DETECTING SURFACE DEFECTS ON A WORKPIECE SUCH AS A ROLLED/DRAWN METAL BAR

CROSS-REFERENCE TO RELATED APPLICATIONS

This application claims the benefit of U.S. Provisional Application Ser. No. 60/430,549 filed Dec. 3, 2002, the disclosure of which is hereby incorporated by reference in its entirety.

STATEMENT REGARDING FEDERALLY FUNDED RESEARCH

This invention was made with United States government support under Cooperative Agreement No. 70NAN-BOH3014 awarded by the National Institute of Standards and Technology (NIST). The United States government has certain rights in the invention.

BACKGROUND OF THE INVENTION

1. Related Field

The present invention relates generally to an imaging system that can image the surface details of a workpiece, such as a rolled/drawn metal bar.

2. Description of the Related Art

Figure 2:
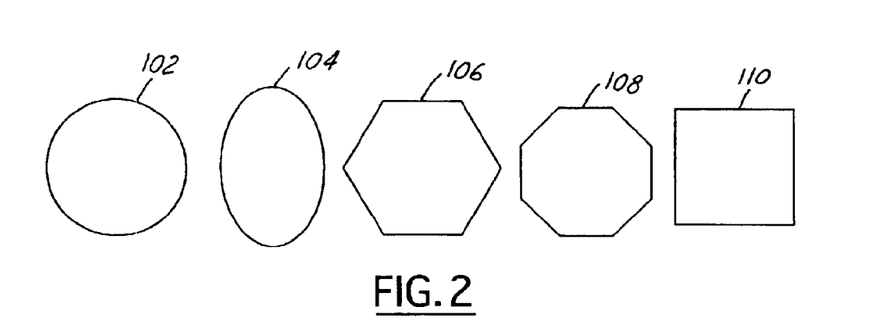
FIG. 2 are cross-sectional views of exemplary geometries for work pieces suitable for inspection by an embodiment according to the present invention.
Figure 3:
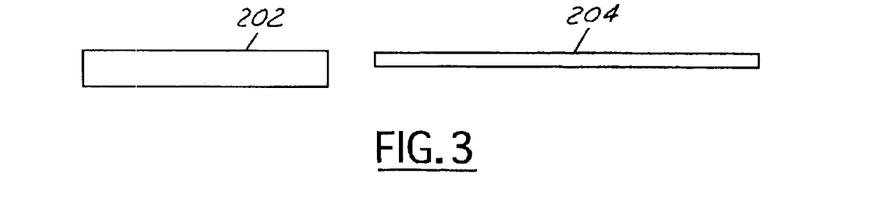
FIG. 3 illustrates a cross-sectional geometry of a metal flat.

It is known to produce a metal bar by a mechanical process such as rolling or drawing. Such metal bar is different than a metal slab, bloom, or strip (hereafter referenced as Metal Flat) in that the cross section of such a bar has a smaller circumference/cross-section-area ratio such that the bar may rotate/twist about a longitudinal axis while moving forward longitudinally. For example, the bar shapes shown in FIG. 2 have a ratio of circumference to cross-sectional-area that is equal to or smaller than 4.25 when the cross sectional area is unity for the given shape. The shape, when taken in cross section, of such a metal bar may be a round shape, an oval shape, or a polygonal shape, as shown as a hexagon, octagon or a square in FIG. 2. A metal bar of this type is typically referred to as "long products" rather than "flat products" in the related industries. Rolling, drawing, extrusion and the like, as used in this disclosure and hereafter referenced as a Reducing Process, describe the ways for reducing the cross sectional dimensions of the metal workpiece through mechanical contact of the applicable tools, such as rollers and drawing dies, and the workpiece. These Reducing Processes are generally continuous, or substantially continuous, in nature.

In the metal production industry, the presence or absence of surface defects is a relevant criterion upon which assessments of the metal products are made. For instance, surface defects account for half of the external rejects (i.e., rejected by the customer) for the steel bar and rod industry. However, the conventional art provides no reliable means to detect such defects. There are several challenges that conventional inspection approaches have been unable to overcome.

First, in the case where inspection occurs while the metal bar products are "hot," the temperature can be as high as 1,100° C., preventing the use of many inspection technologies. Second, the traveling speed of such a metal bar as described above can be, presently, as fast as 100 m/s, several times faster than the speed of the fastest metal strip and nearly 100 times faster than a metal slab or bloom. Further, speed increases are expected in the near future in the range of 150 m/s to 200 m/s. Conventional inspection approaches simply cannot accommodate such high traveling speeds. Third, a high temperature metal bar such as described above is typically confined in a sectional conduit so that the bar will not cobble. Cobbling is an incident wherein a hot, high speed metal bar runs freely outside the conduit. The space, therefore, for any inspection device is extremely limited.

Figure 4:
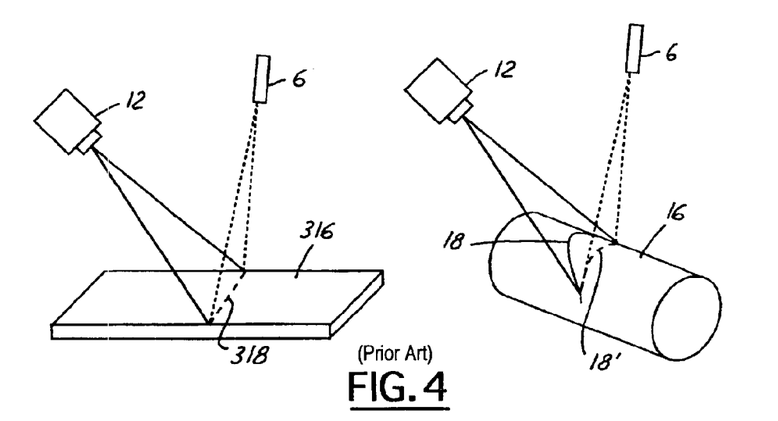
FIG. 4 is a diagrammatic view illustrating a conventional lighting scheme as applied to a metal flat and a bar.

While it is known to apply various imaging approaches to the inspection of cast or rolled Metal Flats, imaging technologies have heretofore not been used in Long Products (i.e., metal bar) inspection. Conventional imaging systems are not believed capable for use in inspecting metal bars and the like because the geometry of the metal bars invalidate the illumination and imaging designs that are used to enhance/capture defects on flat surfaces. FIG. 4 illustrates the differences of applying illumination and of capturing images on a flat workpiece versus a round workpiece. As to the non-flat workpiece, the freedom in optical alignment and optical working ranges disappears when the object of interest does not have a flat surface. For instance, the image line and the illumination line may not overlap if the light or the camera is tilted, as shown in exemplary fashion in FIG. 4. Furthermore, metal bars typically are at a higher temperature than Metal Flats. Heat dissipation of an object is proportional to the area exposed to the cooling media, such as ambient air or water spray. The area of a Metal Flat is several times larger than that of a metal bar, assuming both the flat and the bar are made of the same material and both have the same longitudinal unit density and cross section area.

It is, however, known to employ imaging-based instruments for bar gauge measurement/control (shadow measurement), bar existence/presence, and bar traveling speed measurement in the Reducing Process.

It is also known to employ electromagnetic devices, such as eddy current-based instruments, in the assessment of long products. Eddy-current based sensing systems are used for the detection of surface imperfections in the Reducing Process for in-line inspection. This approach has a high response rate, able to work in a high throughput production line environment (e.g., one kilometer of hot steel bars per minute). However, this approach has several drawbacks. First, it must be very close to the hot surface (typically less than 2.5 mm). Accordingly, it is vibration sensitive and temperature sensitive. Moreover, it is not quantitative in the sense that it is NOT able to describe the nature of the detected defect. Finally, eddy-current approaches are incapable of detecting certain types of defects. As a result, the inspection outcome from eddy current devices is not used by the metal industry for a deterministic judgment on the quality of a specific product. Rather, the output of eddy current-based instruments is only used for qualitative analysis, such as "this batch of steel bars is generally worse than the batch produced last week," in the Reducing Process for process control purposes, for example, only.

Another approach attempted in the art employs ultrasonic sensing. This is an approach to replace the eddy current sensors with ultrasonic ones. However, many of the restrictions associated with eddy current-based instruments, such as the short working distance, apply with equal force.

Other inspection technologies used in the art include magnetic penetrant, circumflux, and infrared imaging with induction heating. The use of these technologies, however, is restricted. First, these techniques can only be used on "cold" metal bars. That is, these technologies cannot be used for in-line inspection during or shortly after hot rolling applications. Also, the metal bars must be descaled before inspection. In addition, the use of magnetic penetrant is messy and cumbersome. This process typically relies on human observation with ultra violet illumination, instead of automatic imaging and detection. The circumflux device is an eddy-current based unit, designed with a rotating detection head. Such rotating mechanism limits the application of this device in metal bar inspection with high traveling speeds, typically used at about 3 m/s. Such device is also expensive due to the moving sensing head design. The combination of induction heating and infrared imaging is based on the fact that induction current is only formed on the surface of the metal bar, and the surface defects on the metal bar will result in higher electrical resistance. Therefore, the spots with surface defects will heat up faster than other areas. There are issues associated with this approach in that (a) such faster heat up is a transient effect and thus timing (time to take images) is very critical; and (b) infrared sensors are not available for very high data rates and therefore cannot support metal bars with high traveling speed.

Of course, inspection is possible after manufacture of the metal bars. However, post-manufacturing inspection often is not possible because the product is so long and coiled up, making the bar surfaces not accessible for cold inspection technologies.

Currently, real-time inspection of metal bars manufactured with Reducing Processes is very limited. Metal bars are generally shipped from the manufacturer to the customer even if defective signals are posted by a conventional in-line eddy current inspection system. Customer complaints may therefore appear 3 to 6 months later due to surface defects on the metal bar products that are not immediately apparent to the customer. Such complaints cost the metal bar suppliers (i.e., manufacturers). The metal bar suppliers will either refund the customers for the entire coil/batch or cost share the expenses of additional labor to inspect the parts made out of the metal bar coil/batch.

There is therefore a need for an apparatus and method to minimize or eliminate one or more of the problems set forth above.

SUMMARY OF THE INVENTION

It is one object of the present invention to overcome one or more of the aforementioned problems associated with conventional approaches for an imaging-based apparatus suitable to be used in-line or off-line to detect surface defects on rolled/drawn metal bars.

The present invention is directed to solving one or more of the problems associated with conventional metal bar inspection systems as well as problems associated with applying metal flat inspection systems to metal bars for non-destructive inspection of surface defects on metal bars through the use of an imaging system.

One advantage of the present invention is that it may be effectively employed in the production of metal bars with the aforementioned characteristics, namely, those that may be at a manufacturing temperature, perhaps even hot enough to produce self-emitted radiation, as well as those subject to rotation relative to a longitudinal axis and may potentially be traveling at a very high speed. Others advantages of the present invention include (i) effectively employed to image and detect defects on non-flat surfaces; (ii) use for inspecting metal bars regardless of its temperature; (iii) use for inspecting metal bars traveling at speeds at or faster than 100 m/s; (iv) providing an increased working distance to the metal bar surface, thus minimizing or eliminating the problems set forth in the Background for eddy-current based instruments; (v) providing an output comprising quantitative data with verifiable defective site images; (vi) inspection of the workpiece even before the scale forms on its surface; (vii) suitable for use in inspection at any stage (between the reducing stands or at the end of the line) in the reducing process, not affected by or relying upon transient effects; (viii) providing real-time or near real-time surface quality information; (ix) providing a system absent of any moving sensing heads, thus minimizing or eliminating the problems of moving components set forth in the Background; and (x) providing a system needing only very small gap (less than 50 mm) capable of operating between metal bar guiding conduit sections. However, an apparatus and/or method need not have every one of the foregoing advantages, or even a majority of them. The invention being limited only by the appended claims.

A system is provided for imaging an elongate bar extending along a longitudinal axis. The system includes an image acquisition assembly, a line light assembly, and a computing unit. The image acquisition assembly has a field of view configured to image a first predetermined width over a circumference of a surface of the bar to define an image belt. The image acquisition assembly is further configured to produce image data corresponding to the acquired image belt.

The line light assembly is configured to project a light line belt having a second predetermined width onto the surface of the bar. The light line assembly is disposed, for example by alignment, relative to the image acquisition assembly such that the image belt is within the light line belt. The light line assembly is further configured such that a light intensity is substantially uniform along the image belt when the light is collected by each of the image acquisition sensors.

Finally, the computing unit is coupled to the image acquisition assembly and is configured to receive image data for a plurality of image belts acquired by the image acquisition assembly as the bar moves along the longitudinal axis. The computing unit is further configured to process the image data to detect predetermined surface features of the bar. In a preferred embodiment, the detected features are surface defects and the image acquisition assembly includes n digital cameras, where n is an integer 3 or greater, arranged so that a combined field of view of the cameras corresponds to the image belt.

A method of imaging a metal bar is also presented.

BRIEF DESCRIPTION OF THE DRAWINGS

The present invention will now be described, by way of example, with reference to the accompanying drawings, wherein like reference numerals identify identical components in the several figures, in which.

DETAILED DESCRIPTION OF THE PREFERRED EMBODIMENTS

Figure 1:
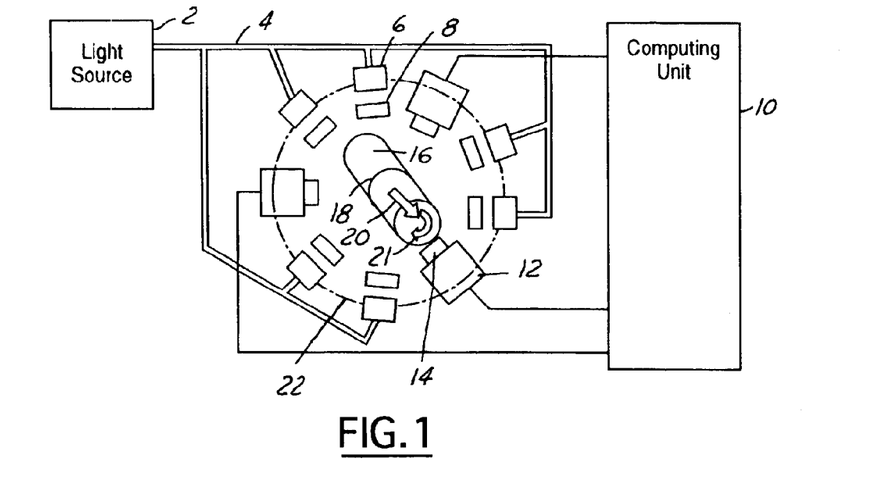
FIG. 1 is a schematic and block diagram view of an embodiment of the present invention.

The present invention permits automated inspection of metal bars for surface defects as the metal bars are being rolled, drawn or the like (i.e., the reducing process described in the Background of the Invention). FIG. 1 schematically illustrates a preferred embodiment in accordance with the present invention.

Before proceeding to a detailed description of the present invention keyed to the drawings, a general overview will be set forth. The present invention provides the following features:

1. Capable of working for metal bars manufactured through reducing processes at different cross section geometry;
2. Capable of working for metal bars in-line at a bar temperature up to 1,650° C.;
3. Capable of working for metal bars traveling at 100 m/s or higher;
4. Capable of detecting surface defects whose critical dimensions are as small as 0.025 mm;
5. Capable of reporting the defect nature such as its size, location (on the bar), image, and the like;
6. Capable of accommodating different sizes of bars, for example only, from 5 mm to 250 mm with minimum adjustment;
7. Capable of providing real-time or near real-time inspection results;
8. Capable of working with a small access window (less than 50 mm) to the target object;
9. No moving parts while inspecting; and
10. Continuous operation in commercial, heavy industrial metal production mills.

FIG. 1 is a simplified schematic and block diagram of a system in accordance with the present invention. FIG. 1 shows line light assembly which may include at least one light source 2, a light conduit 4, a plurality of line lights 6 and a corresponding plurality of optical boosters 8. FIG. 1 further shows a computing unit 10 and an image acquisition assembly that may include a plurality of cameras 12 each having a corresponding lens 14.

Figure 5:
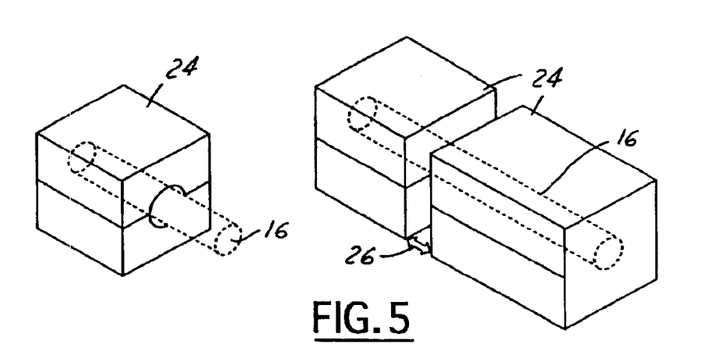
FIG. 5 are simplified perspective views illustrating a bar constrained during its travel by a conduit, and a gap between adjacent conduits in which an embodiment according to the invention may be situated.

With continued reference to FIG. 1, a workpiece or object under inspection, such as an elongated metal bar 16 extending along a longitudinal axis, is shown moving along its longitudinal direction 20 at a speed up to 100 m/s or faster while bar 16 is going through a reducing process. The metal bar 16 may be formed from one selected from the group comprising steel, stainless steel, aluminum, titanium, nickel, copper, bronze, or any other metal, and/or their alloys. The bar 16 may be solid or hollow. Typically such metal bar 16 is traveling inside a conduit, as shown in greater detail as conduit 24 in FIG. 5, not shown in FIG. 1. A gap 26, shown in FIG. 5, is defined between two adjacent conduits 24, and is typically very small, for example between about 20 to 50 mm taken in the axial direction for high-speed transit of metal bars 16. It should be understood that metal bar 16 may be at an elevated temperature, for example as hot as 1,100° C. for a hot rolling process. It should also be appreciated that metal bar 16, given its geometry, is prone to twist/rotate about its longitudinal axis in the direction indicated by arrow 21 in FIG. 1 when it travels in direction 20. This possibility for rotation has, among other items, presented problems for conventional imaging systems. As will be described in greater detail below, the present invention overcomes this problem to provide an imaging system that is robust to twisting and/or rotation.

In order to detect surface defects on bar 16, an imaging system in accordance with the present invention must be provided having certain features, as described below. With continued reference to FIG. 1, the imaging system includes an image acquisition assembly that preferably comprises n imaging cameras 12, wherein n is an integer 3 or greater. The parameter n is selected to be three or higher based on an analysis set forth below. Each camera 12 is arranged so as to cover a circumferential span of at least 120° in order to image the entire surface of bar 16. That is, the image acquisition assembly has a composite or combined field of view configured to image the entire circumference of the surface of the bar 16 to define an image belt 18. As further described below, the image acquisition assembly is further configured to produce image data based on the image belt 18. The analysis for the parameter n for the number of cameras will now be set forth.

Figure 6:
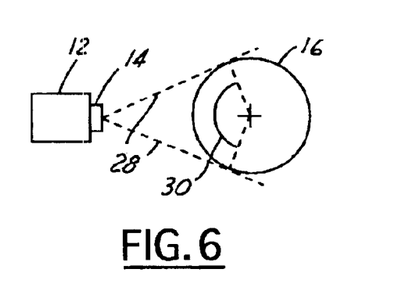
FIG. 6 is a simplified plan view illustrating an imaging coverage on a metal bar using one camera.

As shown in FIG. 6, a regular lens 14 associated with camera 12 will have a viewing angle (field of view) formed by the two tangential lines of sight 28 extending from a focal point of lens 14 to the surface of bar 16. This viewing angle, when projected onto a non-flat surface, such as the one shown in FIG. 6, will result in a circumferential coverage 30 that is less than 180° and will be insufficient to cover 360° with only two lens/camera units where the lens are not telecentric.

Figure 7:
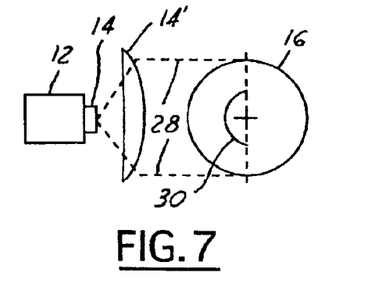
FIG. 7 is a simplified plan view illustrating an imaging coverage on a metal bar with one camera and a telecentric lens.

FIG. 7 shows an arrangement with a telecentric lens 14'. A true telecentric lens, which collects lines of sight that are in parallel, even if used, would not practically provide for a two-lens/camera system because of arc length variation. In particular, the lines of sight 28 are parallel with the addition of telecentric lens 14' to lens 14. In this case, the circumferential coverage 30 is 360°. Theoretically speaking, the entire surface of round shaped bar 16 can be covered using only two lens/camera units. However, as alluded to above, a problem of non-uniform pixel sizes arises.

Figure 8:
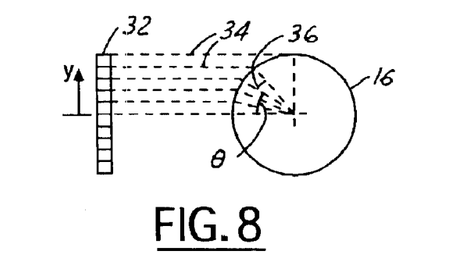
FIG. 8 is a simplified plan view illustrating an arc length variation based on a projection of same size grids, such as a line of pixels, onto a bar profile.

As illustrated in FIG. 8, the evenly spaced lines of sight 34, as derived from an evenly-spaced imaging sensor 32 having a plurality of pixels, can result in an uneven arc length 36 on the surface of bar 16, pixel-to-pixel. Even spacing is a very typical arrangement on an imaging sensor such as a CCD chip. The arc length 36 can be calculated using equation (1) as follows:

$$S = p/\cos(\theta) \qquad \text{EQN (1)}$$

where S is the arc length 36 mapped to the pixel in position y, p is the pitch of the pixel array or the pixel size, and θ is the projected angle that can be derived from $$\theta = \arcsin(y/r), \text{ in which } y \leq r \text{ and } r \text{ is the radius of the metal bar 16.} \qquad \text{EQN (2)}$$

From FIG. 8 one can learn that as y→r, θ→90°. As θ→90°, S the arc length 36 will approach infinity based on EQN (1). In reality, S will still be a finite number. However, S will be substantially (several times) larger than p, the pixel size. That is, the image resolution in this area will deteriorate so much that this approach is infeasible. Note that the same arc length analysis can be applied to the bottom half in FIG. 8, in which case y→−r.

With three cameras, θ can be established at 60°. When θ=60°, S the arc length 36 (at the 12 o'clock and 6 o'clock positions in FIG. 8) is only 2 p, an acceptable and controllable deterioration in image resolution. If better image resolution is desired, four cameras or five cameras, or even more may be used (i.e., the parameter n referred to above can be an integer equal to four, five or greater). All the lens 14/camera 12 combinations, as illustrated in FIG. 1, are preferably arranged such that all such lens/camera combinations are positioned along a circular path 22 that is concentric to the circular geometry of the exemplary metal bar 16 such that the working distances, the distance from each lens 14 to the nearest metal surface, are the same or nearly the same for all the lens/camera combinations. Note that the path 22 may stay circular if the metal bar is non-circular, say a hexagon, for the purpose of generally serving the same manufacturing line. One that is skilled in the art can appreciate that the path 22 can, if desired, be made to conform to the actual bar geometry.

In order to accommodate the potentially very high traveling speed of the metal bar 16, high data rate cameras 12 are preferably used. The cameras 12 in the system are thus preferably digital cameras, with digital outputs to computing unit 10. This digital output format is desirable to accommodate the harsh environment for signal fidelity. This digital format image signal may be received by the computing unit 10 through standard communication channels such as IEEE-1394 (also known as FireWire), Camera Link or USB ports, or a special interface known as a frame grabber. Each camera 12 preferably is able to generate 10,000,000 (or 10 Mega) pixels per second such that a defect feature that is 0.025 mm×0.5 mm can be identified. It should be appreciated, however, that to detect larger features, a reduced resolution, and hence reduced data rate (in pixels per second) would be required. Line scan cameras are preferred even though progressive (non-interlaced) area scan cameras can be used when the bar 16 is not traveling fast. Line scan cameras have an advantage over area scan cameras in that line scan cameras only require a line of illumination, instead of an area of illumination. This will simplify the illumination complexity caused by the non-flat surface. In the case of using line scans, all the cameras in FIG. 1 will be aligned such that their imaging lines will be forming a circumferential ring, an image belt 18, on bar 16. This alignment is necessary to address the issue of twist and/or rotation (item 21). If this alignment is not held, the twisting or rotating motion can result in incomplete coverage of the bar surface.

Referencing back to FIG. 1 again, each camera will have a lens 14 to collect light reflected from the bar surface. Telecentric lenses (lenses that collect parallel image light rays, as illustrated with FIG. 7) are preferred for a more uniform arc length distribution, even though regular lenses can be used. In addition, cameras 12 may be configured to include a lens iris to control exposure, and further, preferably configured (if included) with the use of a predetermined lens iris setting for improved depth of focus/field in the application.

With continued reference to FIG. 1, the imaging system according to the present invention also includes a line light assembly configured to project a light line belt onto the surface of the metal bar 16. Preferably, the line light assembly includes a plurality of line lights 6. These line lights 6 can be individual light sources, such as lasers, or light delivery devices, such as optical fiber lights, as shown in FIG. 1. The light delivery devices must work with at least one light source, as shown in FIG. 1. More than one light source can be used if higher light density is needed for illumination. For metal bars 16 that travel at very high speed, the cameras may be light starved due to very high line/frame rates equating to a relatively short exposure time. An optical booster 8 may therefore be used for each line light to concentrate the light and increase the light intensity. This booster 8 can be a cylindrical lens or a semi-cylindrical lens. To use the imaging system in accordance with the present invention for metal bars 16 that are at an elevated temperature, the line lights and the boosters must be made of special materials configured to withstand such elevated temperatures. Each line light 6, for example, may be configured to have its own glass window to serve this purpose. In the case of optical fiber line light, the material that binds the fibers together must be able to withstand high temperature, such as the high temperature epoxy. The boosters 8 must be made of materials that can withstand high temperature, too. Usable materials include glass, Pyrex, crystal, sapphire, and the like.

Figure 9:
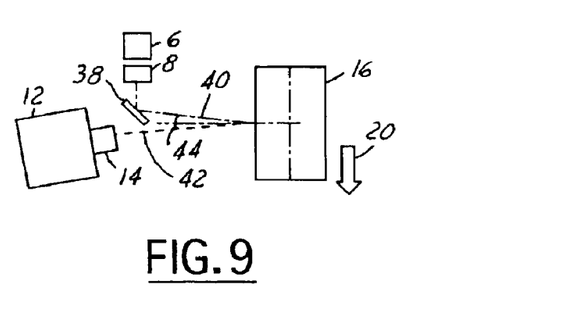
FIG. 9 is a simplified plan view illustrating a lighting arrangement for a bar surface in accordance with the present invention.

FIG. 9 is a top view of the preferred embodiment shown in FIG. 1. To cope with light starving, the alignment between the line lights and the cameras is important. As illustrated in FIG. 9, the surface of metal bar 16 after the reducing process, before, for example, a descaling process, can be treated as a reflective surface. Therefore, the optical law set forth in equation (3) applies:

$$\text{"incident angle=reflective angle"} \qquad \text{EQN (3)}$$

EQN (3) is preferably used in a preferred embodiment to maximize the reflected light that is captured by the plurality of cameras 12. The line lights 6 will each emit the light ray 40, which is boosted by a booster 8 and projected onto the surface of the metal bar 16. The light ray 40 is reflected to the path 42 and received by the lens 14 and eventually by the camera 12. Note that in FIG. 9, the metal bar 16 travels in the direction 20. The projected and reflected light rays 40 and 42 form an angle 44, equally divided by the normal line to the surface of the metal bar 16. This angle 44 must be as small as possible, due to the illumination problem described above that is associated with a non-flat surface, as illustrated in FIG. 4. In FIG. 4, the light line 18' and the image line 18 will not overlap on a non-flat surface. The ideal case is for the angle 44 in FIG. 9 to be 0°. As this is only possible by using a beam splitter, it is less practical to do so when the system is light starving due to inherent power losses imposed by using a beam splitter for example. The highest efficiency a beam splitter can achieve is 25%, assuming a 0% transmission loss. Therefore, the angle 44 is preferably selected so as to be reasonably small, such as 1° or in its neighborhood. If necessary, a reflective mirror 38 can be used to assist in packing the camera and the light for a small angle 44. This is another reason to use line scan cameras in this application. Line scan cameras only need an image path 42 with a small width, such as from 5 to 30 microns. The angle 44 can be kept very small with this small image path feature.

Figure 10:
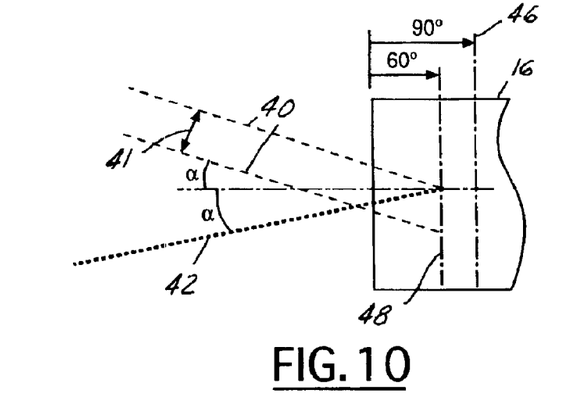
FIG. 10 is a simplified plan view further illustrating, in greater detail, the lighting arrangement of FIG. 9.
Figure 11:
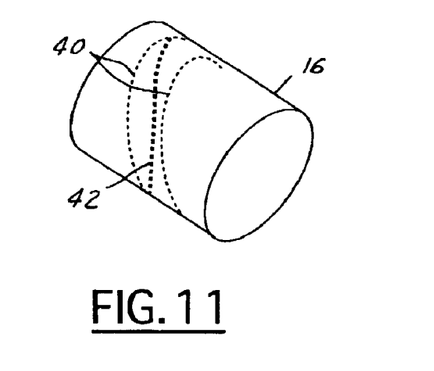
FIG. 11 is a simplified perspective view of a metal bar in connection with which the lighting arrangement of the present invention is used.

FIG. 10 shows in greater detail a portion of the lighting setup of FIG. 9. As mentioned above, the angle 44 will not be 0 degrees unless a beam splitter is used. Therefore, each line light 6 must have a substantial width W (item 41 in FIG. 10). One can see that in FIG. 10 the metal bar 16 has a centerline 46. The line 48 indicates the 60° mark on the bar surface, starting from the tangential boundary on the left hand side of the bar, as shown in FIG. 10, and increasing to the right. One camera must be able to image the metal bar 16 for the upper half to this 60° mark line 48. In a three-camera embodiment, the above calculations apply. If more cameras are used, the line 48 may represent 45° for a four-camera system, at 36° for a five-camera system, and so forth. If designed symmetrically, the camera can also image the bottom half of the metal bar 16 for 60°. In order to achieve this coverage, the light line width W must be greater than a threshold based on:

$$W \geq 2 \cdot r \cdot (1 - \cos 60°) \cdot \sin \alpha \quad \text{EQN (4)}$$

in which r is the bar radius and a is the incident angle (half of the angle 44). The 60° can be replaced by another angle if a different numbers of cameras other than three are used in the inventive imaging system. This notion is further illustrated in FIG. 11, in which the image line 42 is clearly curved differently, yet covered by the light line 40. In other words, the image acquisition assembly (e.g., the plurality of cameras in the preferred embodiment) captures an image belt 18 having a first predetermined width over the entire circumference of the surface of the bar 16. The line light assembly (e.g., the plurality of line light sources in the preferred embodiment) projects a light line belt onto the surface of the bar 16 having a second predetermined width. The line light assembly is disposed and aligned relative to the image acquisition assembly such the image belt falls within the light line belt. Through the foregoing, the problem of non-flat surfaces is overcome.

Figure 12:
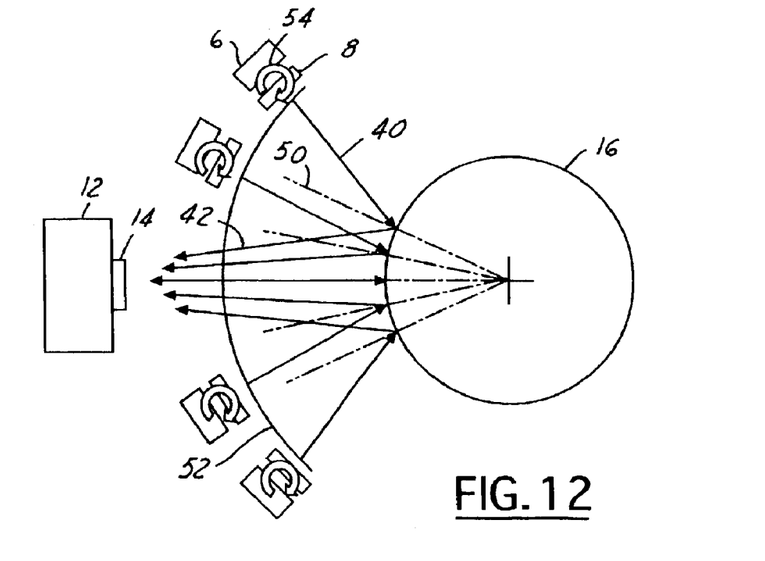
FIG. 12 is a simplified plan view illustrating the lighting arrangement in the circumferential direction as directed toward a bar surface.

Additionally, these line lights must be positioned such that the light intensity as reflected from a point on the bar surface to the camera that covers that point is uniform for all the points on the image belt 18 (FIG. 1). A more detailed illustration is shown in FIG. 12. All the illumination must follow the law described in EQN (3). FIG. 12 illustrates this arrangement for one camera. It should be appreciate that such arrangement may be duplicated for other cameras used in the inventive imaging system. Based on EQN (3), the angle formed by the incident light ray 40 and the reflected light ray 42 must be evenly divided by the surface normal 50. As in FIG. 12, an illuminator 52 preferably includes a curved surface. Illuminator 52 is a device whose emitted light rays (perpendicular to this curved surface at the point of emission) will be reflected by the surface of the bar 16 to the imaging sensor in camera 12 and lens 14 based on EQN (3). Note that curve 52 need not be a circular curve. This curve 52 depends on the distance between the curve 52 and the surface of the bar 16 (i.e., target). Curve 52 may not be a smooth curve if the bar is not circular. Even though an illuminator with curve 52 can be made with modern technologies, such illuminator can only be used with bars 16 at the designated diameter. In some applications it is not practical. An alternative is to simulate such illumination effect with an array of light lines 6 and 8, as shown in FIG. 12. Each combination of light line/booster can be made adjustable such that its direction can be re-pointed as shown by item 54 to accommodate targets with different diameters. The light line approach is also beneficial in the case that the bar 16 is not circular.

Referencing back to FIG. 1, a computing unit 10 is coupled to plurality of cameras 12. The computing unit 10 is configured to receive the image data for a plurality of image belts 18 acquired successively by the cameras 12 as the bar 16 moves along the longitudinal axis in the direction 20 (direction 20 best shown in FIG. 1). Frame grabbers may be used to receive the image signals. The cameras 12 in the system, however, are preferably digital cameras, as described above. The computing unit may comprise one or more computers in order to have enough computing power to process the image data. Image processing hardware may be used in conjunction with the software for faster computing speed. If multiple computers are used, these computers can be linked together through inter-computer links such as TCP/IP or the like.

Figure 13A:
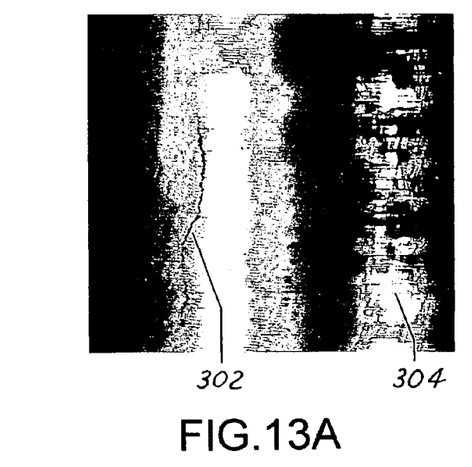
FIG. 13A illustrate a surface defect along with some surface noise.
Figure 13B:
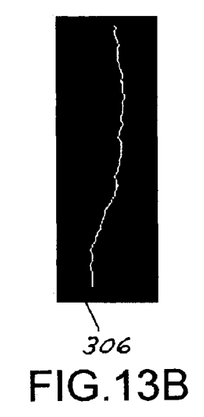
FIG. 13B illustrates an exemplary result of an image processing step according to the invention as applied to the image of FIG. 13A.
Figure 14A:
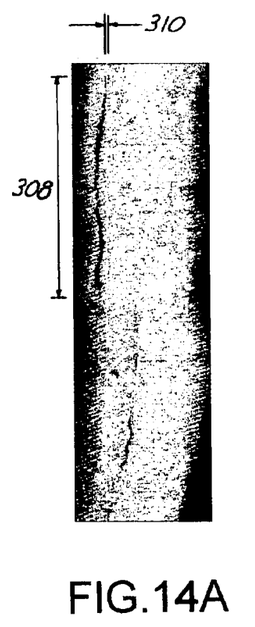
FIGS. 14A–14C illustrate examples of long surface defects that may be found on metal bars and which can be detected by an embodiment according to the present invention.
Figure 14B:
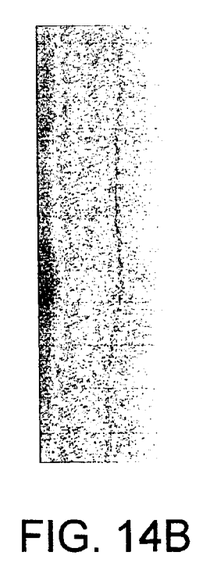
Figure 14C:
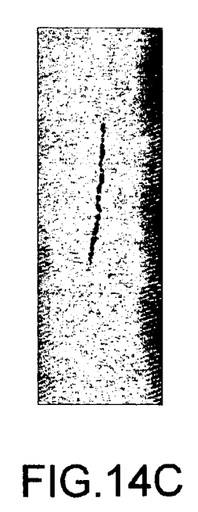
Figure 15A:
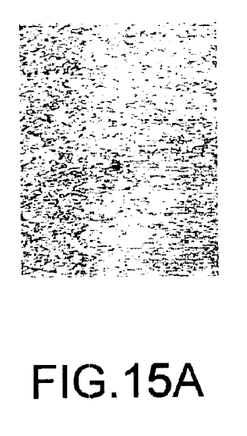
FIGS. 15A–15C illustrate relatively short surface defects that may be found on metal bars and which can be detected by an embodiment according to the present invention.
Figure 15B:
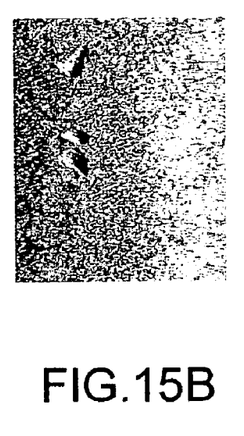
Figure 15C:
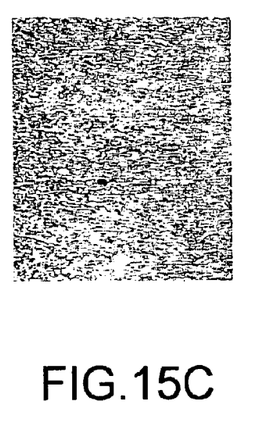

In any event, computing unit 10 is configured to process the image data to detect predetermined features of the surface of bar 16. In a preferred embodiment, the features are surface defects. Thus, the image data will be processed for defects, such defects being shown in exemplary fashion in FIGS. 13A–13B. The images typically contain both the real defects (e.g., item 302) and noise, such as scratch marks (e.g., item 304). Image processing algorithms, implemented in computer codes such as C, C++, machine languages, and the like, or implemented in hardware logic, are used to filter out the noise, and to detect the true defects, as shown in 306. The defects to be identified can be long and have a large aspect ratio, as shown in FIGS. 14A–14C, where item 308 may be 1000 mm long, and item 310 may indicate a width of 0.050 mm. Or, the defects can be short and have a nearly 1-to-1 aspect ratio, as shown in FIGS. 15A–15C. These algorithms are known in the art, but will be described generally. A first layer of processing may involve a comparison of local contrast in the image, such as by comparing a first predetermined threshold to the local contrast. A second layer of processing may involve applying a second predetermined threshold to detect the nature of the defect such as size, location, length and width and the like.

The preferred embodiment described and illustrated in connection with FIG. 1 will also have protection against dust, water, vibrations, and other damaging factors in a typical metal process plant such as a hot rolling mill or a cold drawing mill.

Those skilled in the art shall appreciate the possibility of further restrain the bar and separately using three or more single-camera systems in the reducing process line for inspection.

Those skilled in the art shall also appreciate that covering (e.g., inspection of) a portion of the bar surface less than the entire circumference may be useful enough for statistical process control purpose in the reducing process line.

Those skilled in the art shall also understand that a very high speed (high data rate and high frame rate) area scan camera can be used in place of the line scan cameras if only a certain portion of each of the area scan images is used for processing.

One can also understand that if the metal bars are at an elevated temperature, an optical filter can be used in conjunction with the lens such that only certain wavelengths in the reflected light rays 42 (in FIG. 12) will be used to carry the surface information of the metal bars. Such wavelengths are those not emitted or not dominantly emitted by the metal bars at the said elevated temperature. For metal bars at or colder than 1,650° C., the wavelength 436 nm can be used. In this case, an interference filter at 436 nm will be used with the lens. This wavelength can vary with the temperature. If the temperature decreases, longer wavelength can be used.

In a still further variation, the light line assembly may be configured to include a strobe light, wherein the computing unit 10 synchronizes the illumination (i.e., the strobing) with the image capture function performed by the image acquisition assembly (e.g., the cameras 12 in the preferred embodiment).

In a yet still further embodiment, the computing unit 10 is configured to maintain a running record of the detected defects, including (i) a respective location of each detected defect relative to a "start" position, such as the leading end, on the bar 16 being manufactured through processes that mechanically reduce the cross-sectional area of the metal bars; (ii) a respective notation of the nature of the detected defect, such as the size, shape, contrast; and (iii) optionally, an actual image of the site of and surrounding the detected defect. The record may be useful to the supplier/manufacturer, for example, for determining an up-front discount, and may be provided to the customer (e.g., on a diskette or other electronic means) for use in further processing, for example, what portions of the coil to avoid or do follow-up work on.

We claim:

1. A system for imaging an elongated bar extending along a longitudinal axis, said system comprising:

an image acquisition assembly having a field of view configured to image a first predetermined width over a circumference of a surface of said bar to define an image belt and produce image data corresponding thereto;

a light line assembly configured to project a light line belt having a second predetermined width onto the surface of said bar, said light line assembly being disposed relative to said image acquisition assembly such that said image belt is within said light line belt, said light line assembly being further configured such that a light intensity is substantially uniform along said image belt; and a computing unit coupled to said image acquisition assembly configured to receive image data for a plurality of image belts acquired by said image acquisition assembly as said bar moves along said longitudinal axis, said computing unit being further configured to process said image data to detect predetermined surface features of said bar, wherein said image acquisition assembly includes n digital cameras, where n is an integer 3 or greater, arranged so that a combined field of view thereof corresponds to said image belt, wherein said light line assembly includes a plurality of line light sources each projecting light beams at a first predetermined angle relative to a normal line from the surface of the bar onto which said light beams impinge, and wherein respective principal axes of said cameras are disposed at a second predetermined angle relative to said normal line, said first and second predetermined angles being equal.

2. The system of claim 1 wherein said first and second predetermined angles are about one degree.

* * * * *